United States Patent
Sheesley et al.

(10) Patent No.: US 9,427,774 B1
(45) Date of Patent: Aug. 30, 2016

(54) ULTRAVIOLET-C PHOTOCHEMISTRY FOR CUSTOMIZING AN APPEARANCE OF A WOOD PRODUCT

(71) Applicant: SSB Licensing, LLC, Post Falls, ID (US)

(72) Inventors: David Sheesley, Los Angeles, CA (US); David Seymour, West Hollywood, CA (US); Chris Bartimioli, Post Falls, ID (US); Grover Lee McCollum, Calabasas, CA (US)

(73) Assignee: SSB LICENSING LLC, Post Falls, ID (US)

( * ) Notice: Subject to any disclaimer, the term of this patent is extended or adjusted under 35 U.S.C. 154(b) by 0 days.

(21) Appl. No.: 14/934,114

(22) Filed: Nov. 5, 2015

(51) Int. Cl.
| | |
|---|---|
| *B05D 3/06* | (2006.01) |
| *B05C 15/00* | (2006.01) |
| *A61L 2/10* | (2006.01) |
| *A61L 2/02* | (2006.01) |
| *A61L 2/025* | (2006.01) |

(52) U.S. Cl.
CPC .............. *B05D 3/065* (2013.01); *A61L 2/10* (2013.01); *B05D 3/06* (2013.01); *B05D 3/067* (2013.01); *A61L 2/025* (2013.01)

(58) Field of Classification Search
CPC ........... A61L 2/10; A61L 2/02; A61L 2/025; B05D 3/67; B05D 3/0209; B05D 3/0263; B05D 3/06; B05B 13/0221; B05B 13/0278; B05B 13/08; B05B 13/1214; B05B 13/1292; B05C 13/00; B05C 15/00; B05C 9/14
USPC ...... 118/309, 313, 314, 323, 324, 326, 50.1, 118/620, 668; 250/459.1, 461.1, 503.1, 250/504 R; 422/20, 22, 24
See application file for complete search history.

(56) References Cited

U.S. PATENT DOCUMENTS

| | | | | |
|---|---|---|---|---|
| 6,746,535 B2 * | 6/2004 | Hasenour | ............ | B05B 13/0278 118/309 |
| 8,088,289 B2 * | 1/2012 | Tribelsky | ............... | A23B 7/015 210/748.01 |
| 8,710,460 B2 * | 4/2014 | Dayton | ..................... | A61L 2/10 250/455.11 |
| 9,090,114 B1 * | 7/2015 | Stumm | ................ | B41M 7/0045 |
| 9,132,448 B2 * | 9/2015 | Gunter | ..................... | B05D 3/06 |
| 2005/0230320 A1 * | 10/2005 | Evans | ..................... | A23B 7/015 210/748.11 |
| 2006/0275171 A1 * | 12/2006 | Younts | ...................... | A61L 2/02 422/24 |
| 2011/0253045 A1 * | 10/2011 | Bensen | .................. | D21H 19/14 118/668 |

(Continued)

*Primary Examiner* — David A Vanore
(74) *Attorney, Agent, or Firm* — Mark Farrell; Timberline Patent Law Group PLLC

(57) ABSTRACT

Ultraviolet-C (UVC) photochemistry for customizing an appearance of a wood product is described. In an implementation, a calculated amount of UVC radiation at a wavelength between 100-290 nanometers, for example, is applied to wood to achieve a desired appearance. The customized wood is free of the volatile organic compounds (VOCs) of stains, varnishes, and paints. The amount of UVC radiation to apply can be based on the tannin content of the wood or on other wood parameters or added photoactive agents. Photochemical interaction between the UVC radiation and various wood extracts, metal ion solutions, acids, bases, and oxidizers is also used to modify the color or lightness of a wood product. An example system includes multiple stations for programmatically spraying a wood product with various processing solutions, drying the wood, and irradiating the wood at one or more stages of the process with UVC radiation to interact with both the processing solutions and the wood surface, at programmed time intervals.

15 Claims, 15 Drawing Sheets

(56) References Cited

U.S. PATENT DOCUMENTS

2012/0061586 A1* 3/2012 Yao .................. G01N 21/6456 250/459.1

2013/0300850 A1* 11/2013 Millikan .............. A61B 5/0077 348/77

2015/0259786 A1* 9/2015 Ko ...................... H01L 51/5253 118/50.1

* cited by examiner

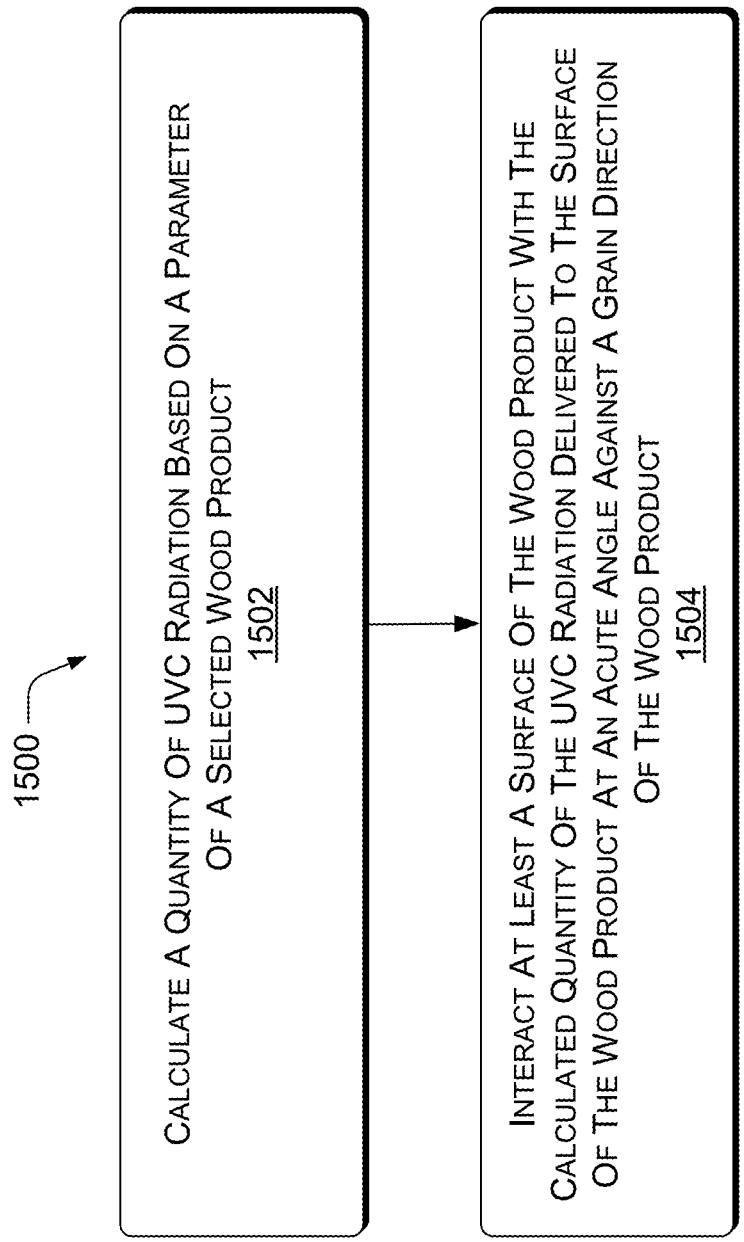

ULTRAVIOLET-C PHOTOCHEMISTRY FOR CUSTOMIZING AN APPEARANCE OF A WOOD PRODUCT

RELATED APPLICATIONS

This patent application is related to copending U.S. patent application Ser. No. 14/934,110 to Sheesley et al., entitled "Ultraviolet-C Photochemistry for Customizing an Appearance of a Wood Product," filed concurrently herewith on Nov. 5, 2015, and incorporated by reference herein in its entirety.

BACKGROUND

Ultraviolet-C radiation (UVC) does not reach Earth's surface from the sun, because all UVC is blocked either by oxygen gas ($O_2$) or by ozone gas ($O_3$) in the atmosphere. All UVC from the sun is completely absorbed by the atmosphere before reaching the surface of Earth, so interaction of solar UVC with living things and with everyday articles, such as wood, is not a natural phenomenon.

Radio waves, microwaves, and infrared light; visible light, ultraviolet light, x-rays, and gamma rays are all electromagnetic radiation (ER) with differences in the wavelength of the ER imparting the vastly different properties of each of these particular types of ER within the ER spectrum. UVC radiation, accordingly, has very unique and specific properties that are uniquely useful in view of the entire ER spectrum, and uniquely useful even compared with other types of UV radiation, such as UVA and UVB. UVC has a higher energy than UVA and UVB, which do reach the surface of Earth from the sun, while UVC does not reach the Earth, as noted above, but can be artificially produced. UVC is electromagnetic radiation with a wavelength between 100-290 nanometers (nm), or in other units, ER with an energy between approximately 4.43-12.4 electron volts (eV). UVC causes damage to the nucleic acids of microorganisms, preventing their replication, thereby destroying the microorganisms as pathogens of human disease. Hence, UVC can be used as a germicidal disinfectant. With its higher energy, UVC can also uniquely drive photolytic, photoreductive, and photooxidative chemical reactions that cannot be driven by UVA and UVB.

Wood that is milled from trees can "weather" when left exposed outside to UVA from the sun. This modification of the color of wood can sometimes be desirable, but takes a long time to achieve, for example six months, when relying on sunlight to provide UVA for discoloring the wood. UVC, however, does not naturally reach the surface of the Earth to modify wood or kill microorganisms, as described above.

SUMMARY

Applying photochemistry of UVC radiation to modify the appearance or custom-color a wood product is described. In an implementation, a calculated amount of ultraviolet-C radiation at a wavelength between 100-290 nanometers, for example, is applied to wood to achieve a desired appearance. The customized wood is free of the volatile organic compounds (VOCs) of stains, varnishes, and paints. The amount of UVC radiation to apply can be based on the tannin content of the wood or on other wood parameters or added photoactive agents. Photochemical interaction between the UVC radiation and various wood extracts, metal ion solutions, acids, bases, and oxidizers is also used to modify the color or lightness of a wood product. An example system includes multiple stations for programmatically spraying a wood product with various processing solutions, drying the wood, and irradiating the wood at one or more stages of the process with UVC radiation to interact with both the processing solutions and the wood surface, at programmed time intervals.

This summary is not intended to identify key or essential features of the claimed subject matter, nor is it intended to be used as an aid in limiting the scope of the claimed subject matter.

BRIEF DESCRIPTION OF THE DRAWINGS

Certain embodiments of the disclosure will hereafter be described with reference to the accompanying drawings, wherein like reference numerals denote like elements. It should be understood, however, that the accompanying figures illustrate the various implementations described herein and are not meant to limit the scope of various technologies described herein.

FIG. 15 is a flow diagram of an example method of modifying an appearance of a wood product by applying UVC radiation to a surface of the wood product at an acute angle against a grain direction of the wood product.

DETAILED DESCRIPTION

Figure 1:
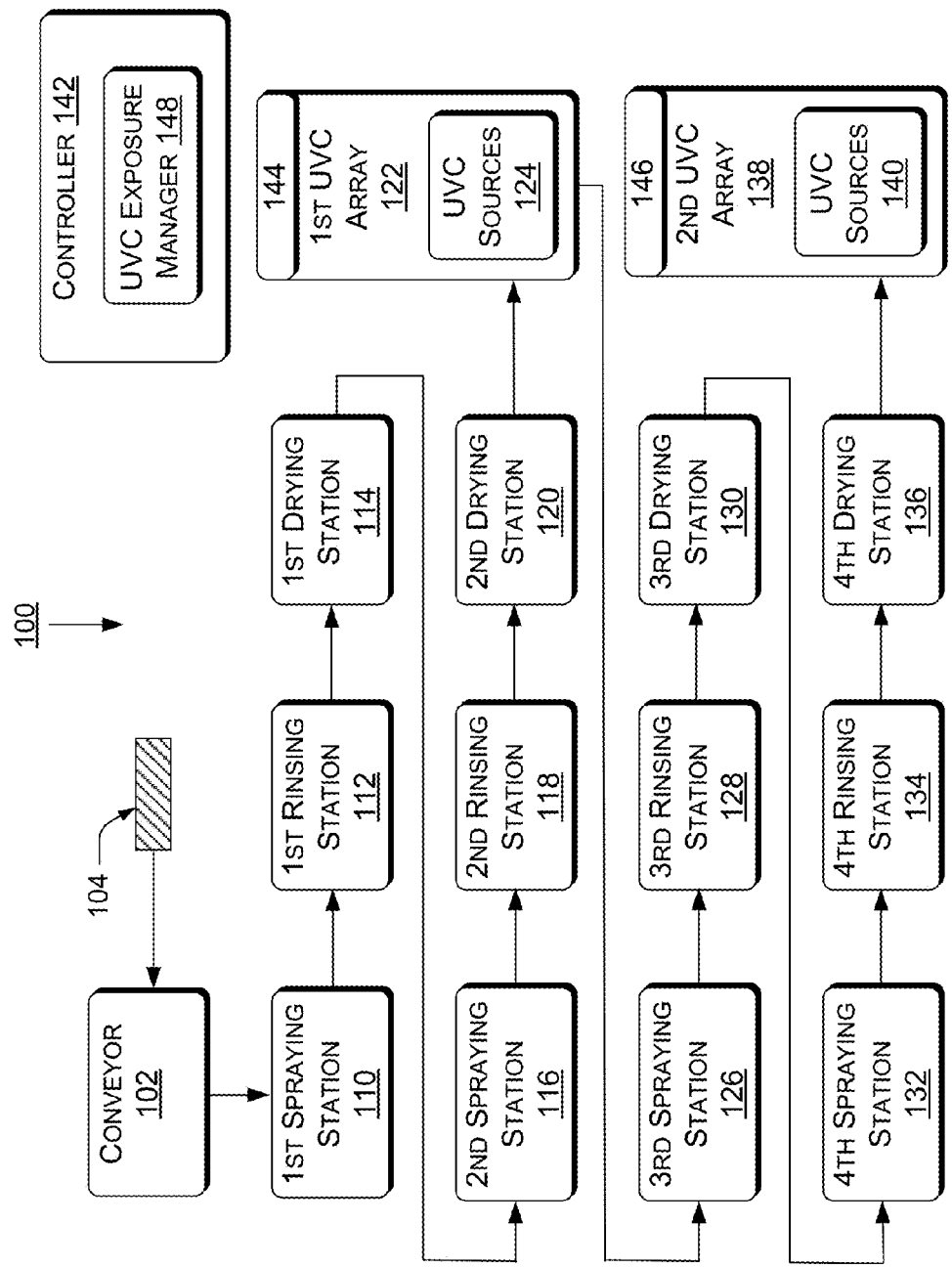
FIG. 1 is a diagram of an example system for applying UVC photochemistry to modify an appearance of a wood product.

In the following description, numerous details are set forth to provide an understanding of some embodiments of the present disclosure. However, it will be understood by those of ordinary skill in the art that the system and/or methodology may be practiced without these details and that numerous variations or modifications from the described embodiments may be possible.

This disclosure describes example systems and methods for applying UVC photochemistry for customizing an appearance of a wood product. For example, UVC can be applied to interact with agents applied to wood and to the wood itself, either raw or modified, to achieve a desired custom-colored, custom-weathered, or custom-aged appearance. The example techniques described herein render a wood product that is free of the volatile organic compounds (VOCs) of stains, varnishes, and paints. At one or more stages of an example process, an example system applies calculated amounts of UVC (at a wavelength around 254 nm, or other UVC wavelengths) at calculated angles and intensities to a wood surface, and to photoactive agents applied to the wood, to achieve a permanent change in appearance, such as a colored, darkened, lightened, aged, burned, antiqued, stained, or a weathered appearance. The amount of UVC to apply can be based on the tannin content of the wood or other wood parameters, either natural or induced, or on characteristics of applied photoactive agents. Photochemical interaction between the UVC, the wood, and various photoactive agents, such as wood extracts, metal ion solutions, acids, bases, and oxidizers can be used to modify the color, lightness, or appearance of a wood product in conjunction with the effects of UVC on the wood itself. An example system may include multiple stations for programmatically spraying a wood product with various processing solutions or otherwise modifying the wood, drying the wood, and irradiating the wood with UVC at one or more stations during the example process, to interact with the processing solutions and the wood surface itself at programmed time intervals.

Selectable Wood Parameters for Interaction with UVC

In a tree, beneath the sapwood is a harder part of the tree known as the heartwood, which is dead, where the xylem tubes have been blocked with resins and gums and have stopped transporting. Wood is often classified into hardwoods and softwoods, although these terms may not refer to actual hardness and softness. Hardwoods are derived from broadleaf deciduous trees that drop their leaves annually, also known as angiosperms because seeds are encased in pods. Hardwoods include ash, beech, birch, hazel, mahogany, maple, oak, teak, and walnut, for example.

Softwoods are derived from evergreen coniferous trees that have needles and cones, which they retain all year, also known as gymnosperms. Examples include cedar, cypress, fir, pine, spruce, and redwood, for example.

Often hardwoods are harder than softwoods, but this is not always the case. For example, balsa wood is a hardwood that is soft. Hardwoods have grains that are desirable for making furniture and woodwork. Softwoods generally come from tall, straight trees, with grains suited for lumber, planks, and poles for supportive construction.

Various parameters of these different kinds of wood may determine the photochemistry of UVC best suited to making a desirable custom-color for the wood. All wood consists of plant cells made of about 50% cellulose, 20-33% lignin, and the rest hemicellulose. Cellulose fiber is roughly the bulk of a tree, while lignin is the adhesive that holds the fibers together. The structure of a specific tree gives wood its constitution—its appearance, behavior, and possible uses. There are hundreds of species of trees, so there are numerous parameters of a wood surface that affect interaction with UVC.

For example, oak has a higher tensile strength than many other woods, making it useful for heavy loads and giving it a characteristic outer appearance. Factors such as how well-seasoned (wet or dry) a particular piece of wood is and the density of the wood also affect its interaction with UVC.

Wood can last hundreds even thousands of years, when properly preserved. Since wood is a natural material it is subject to natural forces of decay through rotting, in which organisms such as fungi, and insects such as termites and beetles gradually eat away the cellulose and lignin. The example systems described herein can also sterilize a wood product from the outset with UVC, while also achieving a desired appearance of the wood product.

Wood is also hygroscopic, absorbing a certain amount of water. Thus, the wood may swell up when damp or wet, releasing the water again when dry air is near and at higher temperatures. Some types of wood can absorb several times their own weight in water, absorbed by the same structures that transported water between roots and leaves when the tree was alive. The amount of water presently held by a wood can modulate the interaction of UVC on the surface of the wood, and can be used to control UVC coloration of the wood or lightening/darkening of the wood. The wetness of the surface of the wood can also modulate the interaction of UVC with added chemical agents applied for interaction with the UVC radiation. The ability of the wood to absorb water (or alcohol or oils) is useful in the example system for getting the wood to absorb water-based (or alcohol-based, oil-based) agents for modifying the surface appearance via the UVC radiation, such as wood extracts, tannins, tannic acid, acids, bases, oxidizers, and metal ion solutions.

Naturally occurring UV radiation at the Earth's surface (having UVA and UVB wavelengths) reacts very little with the surface of wood to change its appearance over a long time (i.e., weathering). This natural process is not very efficient or controllable, and may take up to six months to observe significant results. For practical purposes, wood is resistant to natural UVA and UVB and there is little or no change in the wood, especially in the short term.

UVC, however, does not naturally occur at the Earth's surface. An example process described herein applies UVC, which has a higher energy than UVA and UVB, to alter the appearance of a wide range of wood products, including lumber of various species of tree, to achieve a desired appearance by a controlled process that is much faster than natural weathering that consists of natural UVA exposure.

The example process utilizing application of UVC radiation can also photochemically accelerate other chemical reactions that can be used as wood treatments for achieving coloration, ebonization, and so forth, of the wood surface. Ebonization is a treatment used to darken wood by treating it with iron salts and tannins. A process of interacting UVC with added metal ions and/or tannins on the wood offers a unique process that affects the appearance of the lumber quickly, and in a controlled manner. Likewise, a process of interacting UVC on wood extracts on the wood also offers a unique process that affects the appearance of the lumber quickly, and in a controlled manner. Extracts are wood product solutions, for example, in an aqueous or alcohol solvent system that contains one or more of the following: tannins, tannic acid, wood lignins, cellulose, and wood oils. The extracts may contain other chemicals that are specific to the wood species of origin.

Example Systems

FIG. 1 shows a diagram of an example for applying UVC photochemistry to customize an appearance of a wood product. In an implementation, the example system 100 has a conveyor 102 for transporting a wood product 104 between stations of the example system 100. Not all stations of the example system 100 need to be used for a particular process. For example, in a simple process, the conveyor 102 of the example system 100 conveys the wood product 104 to an array 122 of UVC sources 124, and a calculated amount of UVC radiation from the UVC sources 124 modifies an appearance of the wood product 104. In an implementation, an array 122 of 40 watt UVC tubular bulbs as the UVC sources 124 provides approximately 27-2400 $\mu W/cm^2$ UVC at a 6 inch distance from the surface of the wood product 104.

In an implementation, a more comprehensive example system 100 includes a first spraying station 110 that may apply water or another preliminary agent to the wood product 104. The first spraying station 110 may be followed by a first rinsing station 112 and a first drying station 114. A second spraying station 116 may apply a chemical pretreatment to the wood product 104. The second spraying station 116 may be followed by a second rinsing station 118 and a second drying station 120.

In an implementation, the second spraying station 116, second rinsing station 118, and second drying station 120 are followed by a first UVC reactor (or chamber) at a first irradiating station, including at least one UVC array 122 having UVC sources 124. A third spraying station 126 may apply a first photoactive agent, for example, such as a tannin solution, wood extract solution, etc., to the wood product 104. The third spraying station 126 may be followed by a third rinsing station 128 and a third drying station 130. A fourth spraying station 132 may apply a second photoactive agent, such as a metal ion solution, to the wood product 104. The fourth spraying station 132 may be followed by a fourth rinsing station 134 and a fourth drying station 136. In an implementation, the fourth spraying station 132, fourth rinsing station 134, and fourth drying station 136 are followed by a second UVC reactor (or chamber) at a second irradiating station, including at least one UVC array 138 having UVC sources 140. The example system is managed or controlled by a controller 142, to be described further below.

Each of one or more irradiating stations includes a UVC reactor, chamber, or array 122 & 138 that applies quantities of UVC radiation to a surface of the wood product 104 and to applied photoactive agents, if present, to modify an appearance of the wood product. In an implementation, the quantities of UVC to apply at the irradiating stations are calculated and/or modulated by the controller 142.

In an implementation, each irradiating station comprises an array 122 & 138 of UVC sources 124 & 140, such as multiple tubular 40 watt mercury vapor lamps or bulbs (e.g., 4 feet long) placed adjacently in each array 122 & 138 (e.g., 7-14 bulbs per array 122 & 138) to provide the calculated amount of UVC radiation at a wavelength of approximately 253.7 nanometers. The UVC sources 124 & 140 in the arrays 122 & 138 may also be other types of mercury vapor lamps, or arrays of light emitting diodes (LEDs), for example an array of LEDs providing 278 nm radiation (e.g., LG Innotek, Seoul, Korea; or Sensor Electronic Technology, Inc, Columbia, S.C., U.S.) or one or more UVC lasers (e.g., Sharp Laboratories of Europe, Ltd, Oxford, UK), or UVC flash lamps, UVC pulsed fiber lasers, UVC laser diodes, carbon arc UVC sources, and so forth.

Germicidal UVC lamps may also be used to produce a certain output of UVC energy (for example, 16,000 microwatt seconds per square centimeter—but some units may provide a higher output.) The exposure to UVC radiation may consist of the mathematical product of time duration and a UVC radiation intensity factor.

The UVC lamps in the example UVC reactor may be low-pressure mercury vapor lamps with a strong emission line around 254 nm. Example UVC lamps may also be either amalgam or medium-pressure lamps. Low-pressure UVC lamps offer high efficiencies (approx 35% UVC) but lower power, for example 1 watt per cm power density (power per unit of arc length). Amalgam UVC lamps are a higher-power version of the low-pressure lamps. These operate at higher temperatures and have a lifespan of up to 16,000 hours. Their efficiency is slightly lower than that of conventional low-pressure lamps (approx 33% UVC output) and power density is approximately 2-3 watts per square cm. Medium-pressure UVC lamps have a broad and pronounced peak-line spectrum and a high radiation output, but lower UVC efficiency of 10% or less. Power density of these can be 30 watts per cm or greater.

The example system may further include aluminum reflectors 144 & 146 to reflect and concentrate the UVC radiation to the wood product 104 and the photoactive agents.

In an implementation, the example system 100 includes the arrays 122 & 138 of UVC radiation sources 124 & 140, the conveyor 102 for transporting the wood product 104 under the arrays 122 & 138 of UVC sources 124 & 140, and an exposure manager 148 in the controller 142 for calculating at least one quantity of UVC to interact with a surface of the wood product 104 via the UVC arrays 122 & 138 for modifying an appearance, color, texture, lightness, contrast, reflectivity, grain feature, or knot feature of the wood product 104.

The example system 100 may include the first spraying station 110 for applying water to the wood product 104 prior to interacting the surface of the wood product 104 with a first quantity of the UVC radiation.

The second spraying station 116 may apply at least one pretreatment solution to the surface of the wood product 104, after which the surface of the wood product is irradiated with UVC from the first array 122 of UVC sources 124. The pretreatment solution can be, for example, a NaOH solution, a KOH solution, a hydrogen peroxide solution, a mineral acid, such as sulfuric acid, concentrated sulfuric acid, fuming sulfuric acid, nitric acid, hydrochloric acid, hydrobromic acid, hydroiodic acid; strong, moderate, and weak organic acids, such as acetic acid, glacial acetic acid, carboxylic acids, sulfonic acids; or other chemical or biological agents. A 3-35% hydrogen peroxide pretreatment solution, for example, can be irradiated with UVC radiation to photolytically generate hydroxyl radicals for oxidizing the wood product prior to other treatment steps.

The third spraying station 126 may apply a first photoactive agent to the surface of the wood product 104 after the surface of the wood product 104 has interacted with the first quantity of the UVC radiation. The first photoactive agent may be a tannin solution, a tannic acid solution, a wood lignin solution, a wood extract solution, a cellulose solution, a wood oil solution, or other chemical agent.

The fourth spraying station 132 may apply a second photoactive agent to the surface of the wood product 104 prior to interacting the surface of the wood product 104 with a second quantity of the UVC radiation from the second array 138 of UVC sources 140. The second photoactive agent, for example, may be a metal ion solution, an iron ion solution, a copper ion solution, a manganese ion solution, a nickel ion solution, a chromium ion solution, a calcium ion solution, a magnesium ion solution, a silver ion solution or colloid, a zinc ion solution, a cobalt ion solution, or other chemical agent.

Between these various spraying stations 110 & 116 & 126 & 132, there may be interposed rinsing stations 112 & 118 & 128 & 134 and drying stations (e.g., fans, heaters, infrared radiators) 114 & 120 & 130 & 136 depending on the particular desired process and its programming.

The example system 100 can be composed of more stations or less stations than the example system 100 shown and described. For example, an example system 100 may have more than four spraying stations and more than two irradiating stations.

Figure 2:
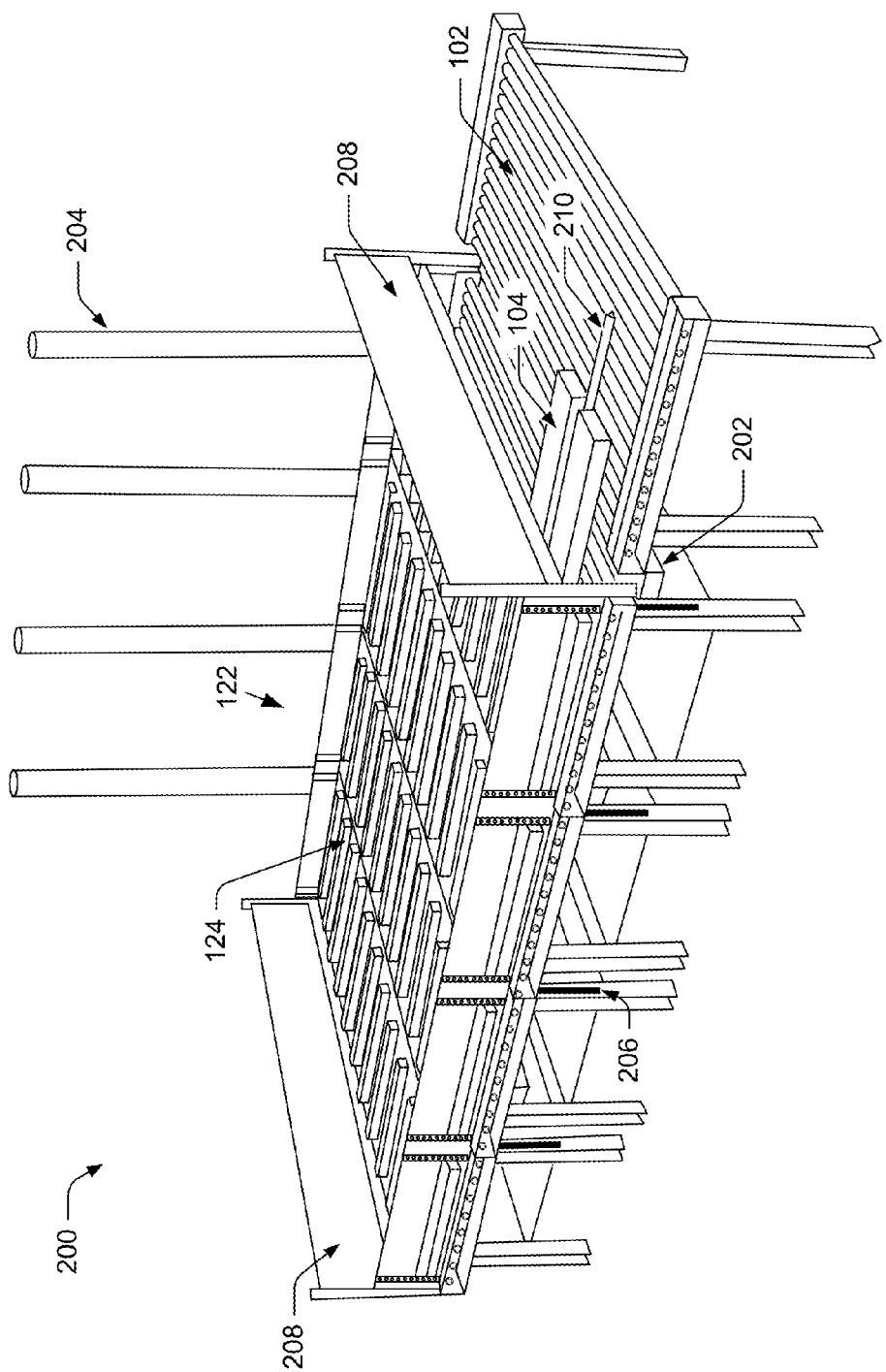
FIG. 2 is a diagram of an example irradiating station of an example system.

FIG. 2 shows an example irradiating station 200 of an example system 100 with a relatively wide conveyor 102 for large wood products 104 such as lumber, boards, and paneling. An example UVC array 122 has tubular UVC sources 124 secured parallel to each other lengthwise for delivering UVC radiation to the wood products 104.

The example irradiating station 200 has optional exhaust blowers 202 for the UVC arrays 122 and exhaust ducts 204 to remove vapors and excess heat. Hydraulic cylinders 206 are remotely controlled to raise and lower one or more arrays 122 of UVC sources 124 to select the distance between the UVC sources 124 and a surface of the wood product 104, thereby providing one mechanism among many possible for selecting the intensity of the UVC radiation on the wood product 104.

In an implementation, the example irradiating station 200 may have automatic doors 208 on each end, thereby forming a closed chamber when the arrays 122 are in operation. The automatic doors 208 can be mirrored, for example with polished aluminum, to reflect the UVC radiation back onto the wood products 104. The automatic doors 208 can also contain the UVC radiation within the example irradiating station 200, thereby shielding humans from potentially damaging effects of UVC radiation exposure.

In an implementation, the example irradiating station 200 may also utilize portable edge mirrors 210 (e.g., aluminum with a triangular cross-section) to reflect UVC to sides of a wood product 104.

The example irradiating station 200 may include various other sensors and control mechanisms, such as temperature sensors to control exhaust blowers 202 and prevent overheating during operation.

Figure 3:
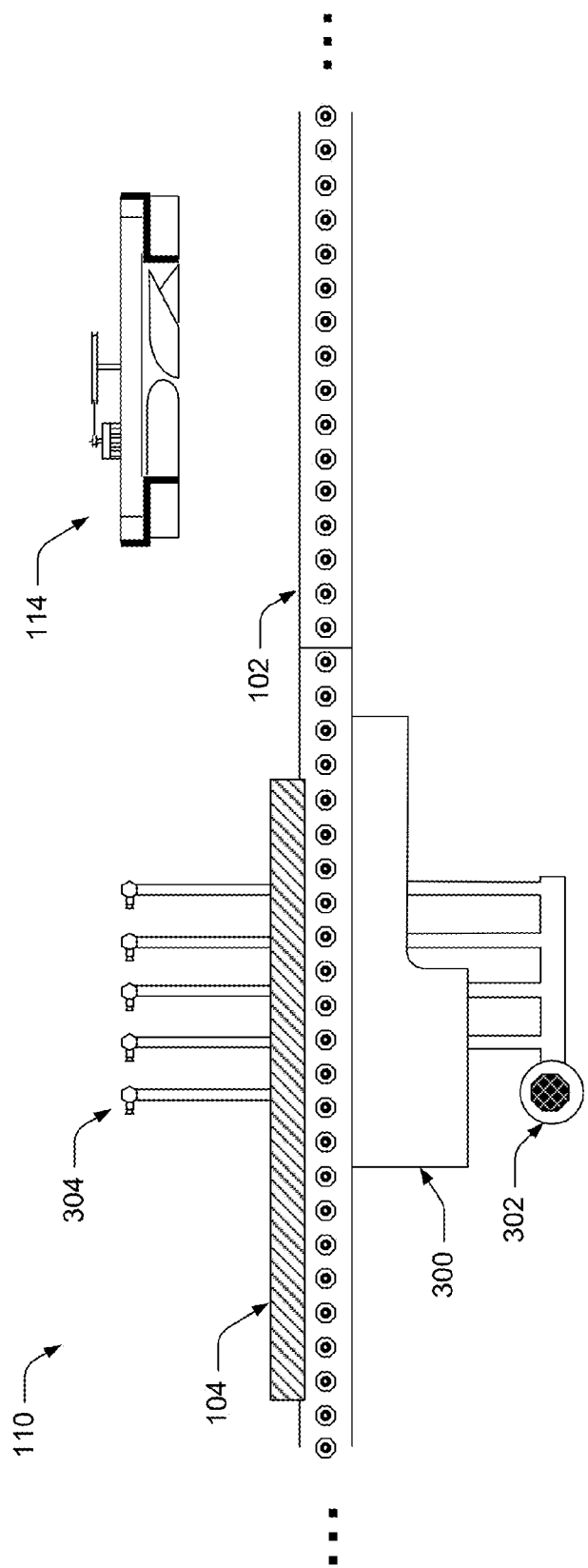
FIG. 3 is a diagram of an example spraying station and drying station of an example system.

FIG. 3 shows an example spraying station 110 of the example system 100. An example spraying station 110 may have a solution reservoir 300, and a pump 302 that transports a fluid, such as water or a photoactive agent, through one or more spray nozzles or jets 304 for application of the fluid to the wood product 104. The conveyor 102 may stop transport of the wood product 104 under the one or more spray jets 304, or may transport the wood product 104 at a uniform speed under the spray jets 304. The spraying station 110 may include, or be adjacent to, a rinsing station 112 (not shown), and a drying station 114, which may include one or more fans and/or heaters.

Figure 4:
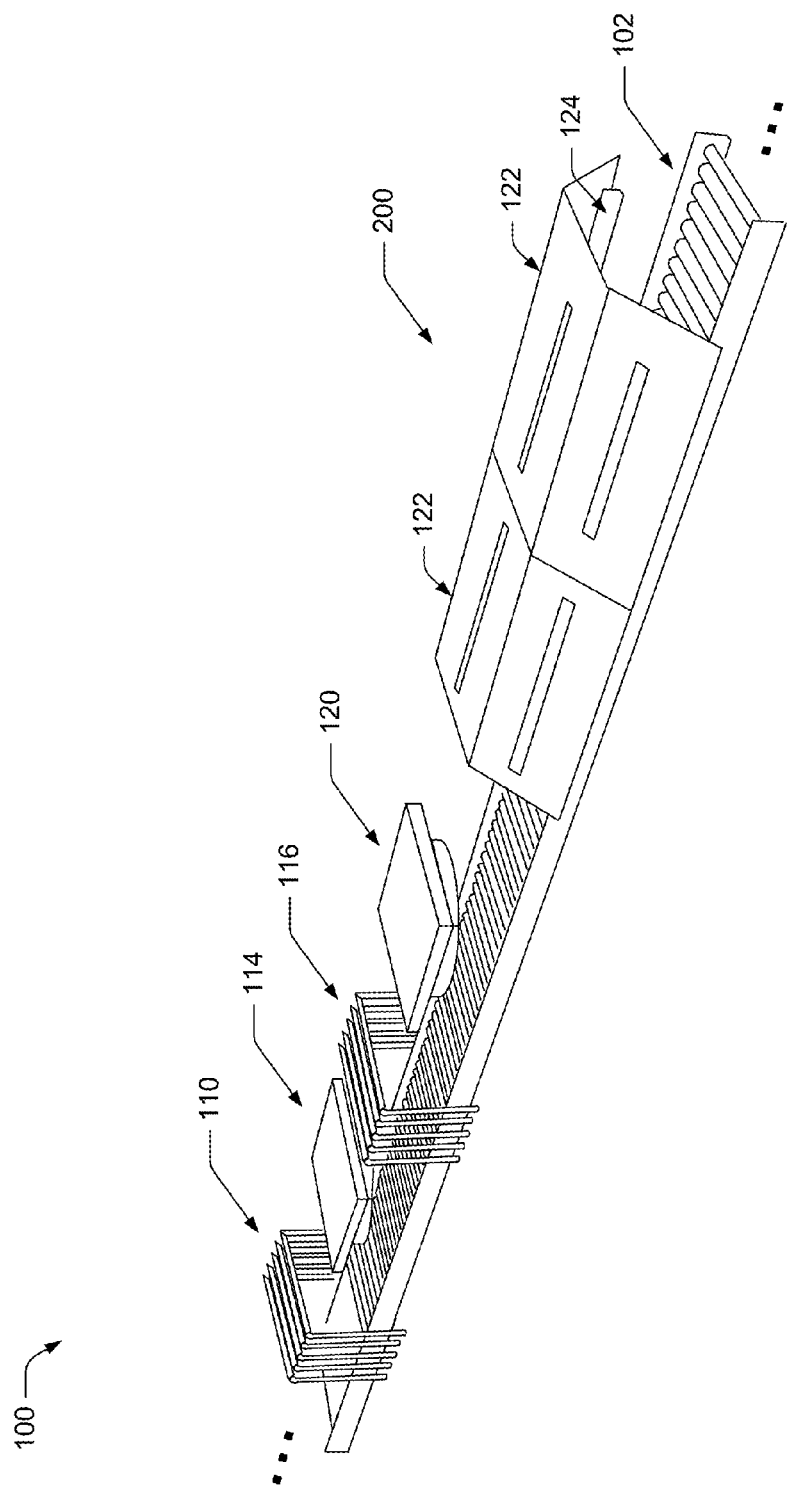
FIG. 4 is a diagram of an example system with multiple stations.

FIG. 4 shows an example implementation of part of the example system 100. A conveyor 102 transports a wood product 104, e.g., from left to right in FIG. 4. In sequence, the wood product 104 is transported through a first spraying station 110, a drying station 114, a second spraying station 116, a second drying station 120, and a first irradiating station 200 including one or more arrays 122 of UVC sources 124.

In an implementation, the UVC arrays 122 of the irradiating station 200 are shaped to wrap around the wood product 104, either partially or entirely. The wrap-around shape of the example UVC arrays 122 in FIG. 4 provides exposure of many sides of the wood product 104 to UVC radiation from many different angles, for efficient overall treatment. Optionally, some of the UVC sources 124 within a UVC array 122 may be turned off, in order to direct the UVC radiation from only UVC sources 124 located on sides of the example UVC arrays 122. Such side-angle UVC radiation can be directed at a surface of the wood product 104 from various selected side angles, such as a Brewster's angle or another angle for efficient use of energy or for special effects. A Brewster's angle can minimize reflection losses at the interfaces between air and some aspects of the surface of the wood product 104. The Brewster angle may need to be calculated to account for the wavelength of the UVC radiation in use and the characteristics of the wood surface. Likewise the UVC radiation may be directed by the arrays 122 at an acute side angle to a surface of the wood product 104 in order to impinge crosswise, against the grain direction of the wood for special effects, such as irradiating only one side of a protruding or bas-relief wood grain.

Figure 5:
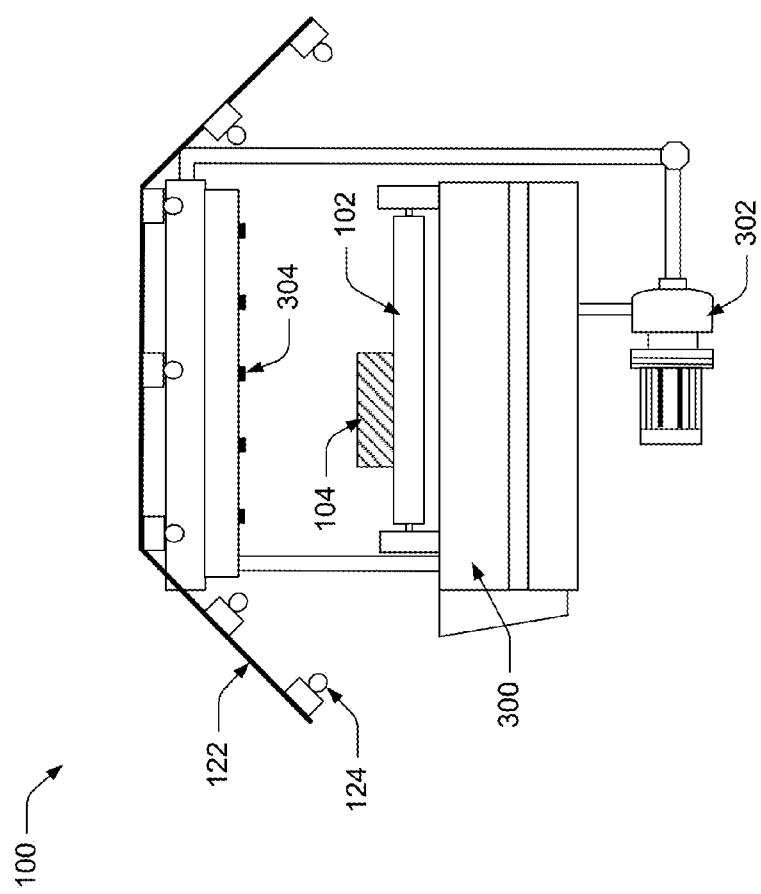
FIG. 5 is a cross-sectional diagram of the example system of FIG. 4.

FIG. 5 shows a cross section of the example system 100 shown in FIG. 4. A wood product 104 is transported by the conveyor 102 under spray jets 304 for application of fluid agents impelled by a pump 302 from a reservoir 300. A UVC array 122 includes individual UVC sources 124 for irradiating the wood product 104 and for irradiating the fluid agents for modifying an appearance of the wood product 104.

The quantity of UVC radiation to be applied can calculated by the exposure manager 148 to sufficiently interact with the surface of the wood product 104 and with the first photoactive agent and/or the second photoactive agent to achieve the desired appearance of the wood product 104.

The quantity of UVC radiation can also be calculated to destroy living microorganisms on the surface of the wood product, including microbes, fungi, molds, bacteria, and viruses to prevent biological destruction of the wood and to stop living pathogens from causing human disease. For example, in an implementation, the UVC can disinfect and sterilize the wood product 104 of 99.99% of pathogens within seconds, including microbes, fungi, molds, bacteria, and viruses.

Figure 6:
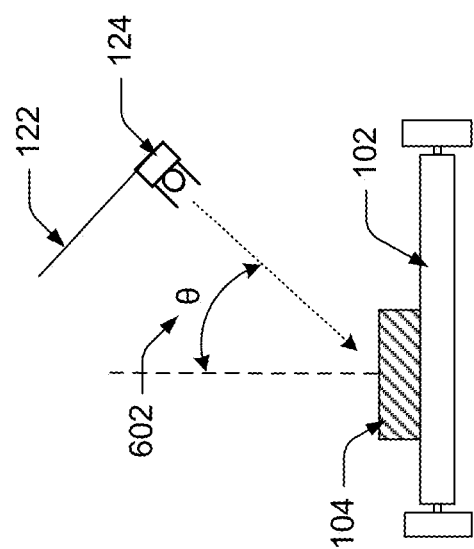
FIG. 6 is a diagram of an example UVC source directing UVC radiation at a surface of a wood product at a Brewster's angle.

FIG. 6 shows an implementation of an array 122 in which the source 124 is disposed or controlled to deliver the UVC radiation primarily at a Brewster's angle 602. Such a delivery configuration can maximize the effects of the UVC radiation in spite of an air-wood interface that can reflect some of the UVC radiation. The UVC delivery at a Brewster's angle 602 can maximize UVC transmittance at the air-wood interface, and minimize the energy used to create a desired effect on the wood product 104, because more of the UVC radiation reaches the wood itself. This implementation can work well will flat wood products 104 and especially with polished wood surfaces.

Figure 7:
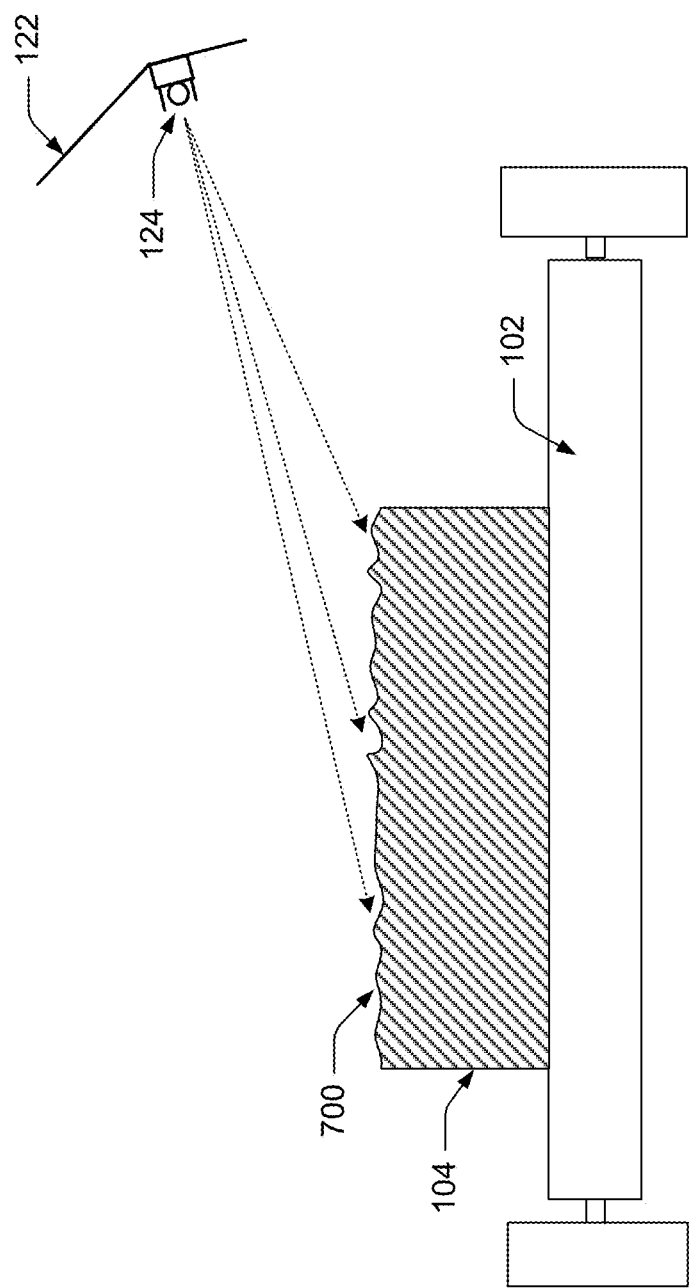
FIG. 7 is a diagram of an example UVC source directing UVC radiation at a surface of a wood product against the grain direction of the wood product.

FIG. 7 shows an implementation of the arrays 122 & 138 of the UVC radiation sources 124 & 140, in which the arrays 122 & 138 of the UVC radiation sources 124 & 140 are disposed to deliver the UVC radiation at an acute angle against the direction of a grain 700 of the surface of the wood product 104. This cross-grain impingement of the UVC radiation can provide special shadow effects when the grain 700 of the wood product 104 is pronounced. In other words, only one side of the grain 700 interacts with the UVC radiation, while the other side of the grain 700 does not.

Figure 8:
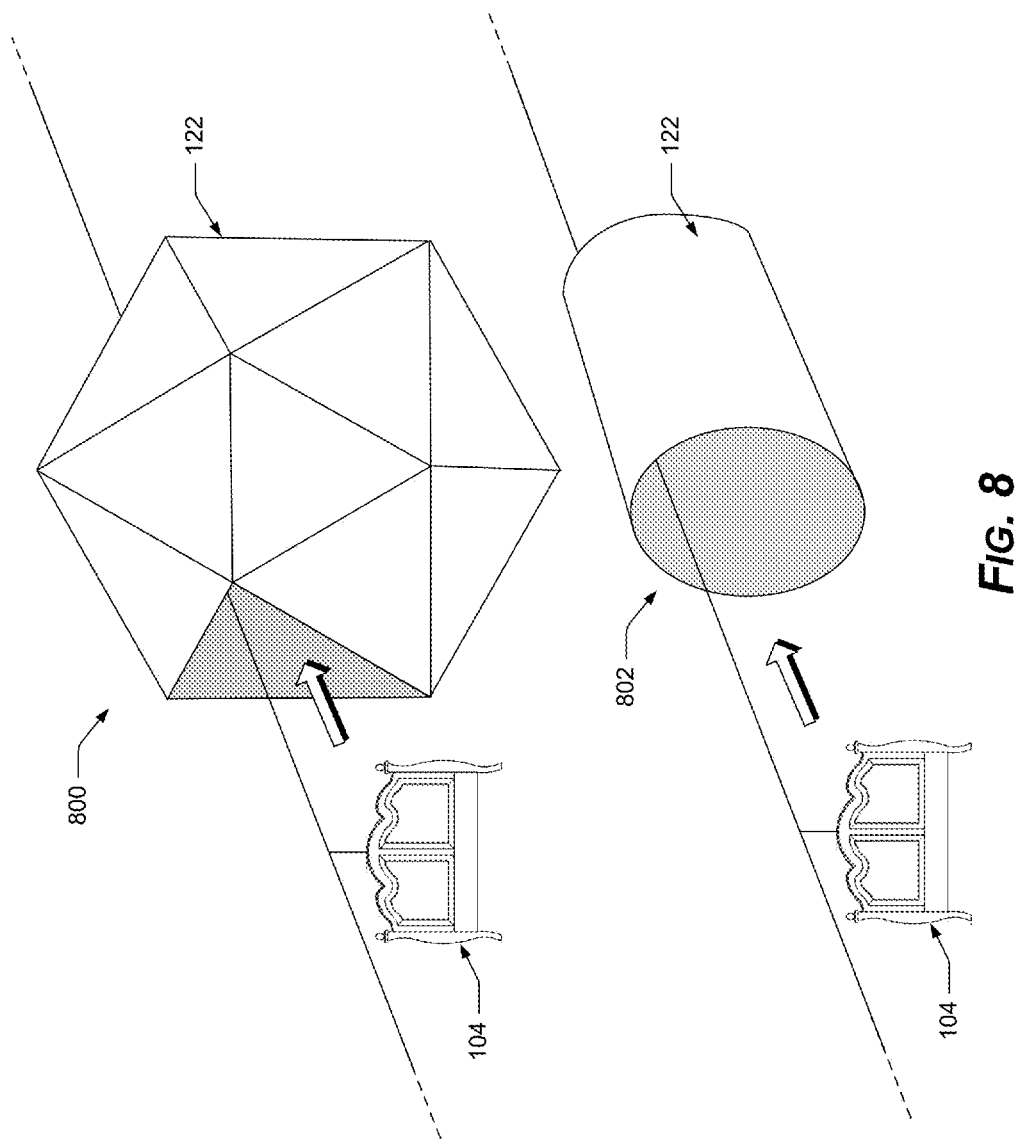
FIG. 8 is a diagram of various example UVC array shapes for applying UVC radiation to multiple sides of a wood product at multiple angles.

FIG. 8 shows an example UVC reactor, in which a geodesic chamber 800 secures the array 122 of the UVC sources 124 at different angles with respect to the wood product 104. For any one surface of the wood product 104, the UVC radiation arrives from numerous different angles, and the geodesic chamber is also capable of directing UVC radiation to expose multiple sides of a 3-dimensional wood product 104 at once, thereby treating an entire wooden object in one pass. Likewise, a 180 degree or 360 degree tunnel chamber 802 may also irradiate all sides of a 3-dimensional wooden object. In each case, the conveyor 102 can be configured to allow the UVC radiation to reach most or all sides of the wooden object, for example, the conveyor may be a cable from which the wooden object hangs, instead of rollers, etc.

Figure 9:
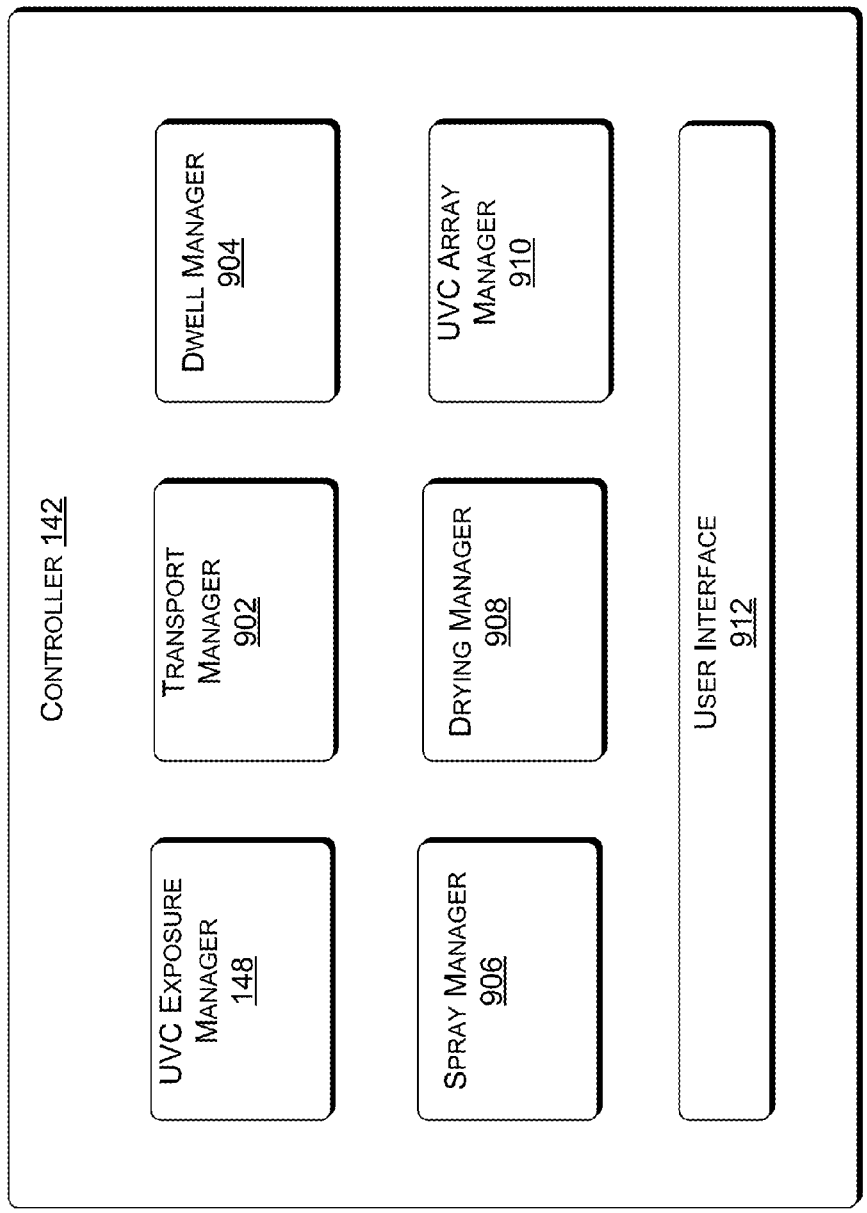
FIG. 9 is a block diagram of an example controller of the example system.

FIG. 9 shows the example controller 142 of FIG. 1, in greater detail. The example controller 142 may consist of computing hardware and programming instructions, such as can be implemented in a desktop computer, mobile computer, smart phone, tablet, etc. Such computing hardware may include a microprocessor, memory, data storage, drivers, interfaces for digitally communicating with analog controllers; and user interfaces. The example controller 142 can also be implemented as a programmable microcontroller.

In an implementation, the example controller 142 includes the exposure manager 148, a transport manager 902 for controlling a speed of the conveyor or conveyors 102 for moving the wood product 104 to the stations of the example system 100, and a dwell manager 904 for stopping or slowing the transport of the wood product 104 for respective time intervals at each relevant station of the example system 100.

The example controller 142 may also include a spray manager 906 for controlling a timing and a duration of applying various agents at each spraying station 110 & 116 & 126 & 132 of the example system 100.

The example controller 142 may also include a drying manager 908 to control timing and volumes of airflows and/or heat at one or more drying stations 114 & 120 & 130 & 136 of the example system 100.

The example controller 142 may also include an array manager 910 for controlling a timing, an intensity, and a duration of the UVC radiation applied to the surface of the wood product 104 at each irradiating station based on the quantity of UVC calculated by the exposure manager 148.

The example controller 142 may include at least one user interface 912 for monitoring the example system 100 and for programming control of the example system 100.

The UVC exposure manager 148 manages the total amount of UVC energy (number of photons, e.g., at 253.7 nm) delivered to a wood surface at each irradiating station. Thus, the UVC exposure manager 148 provides controllable and reproducible results. The UVC exposure manager 148 can manage an intensity of the UVC radiation, and a duration of a UVC radiation application or exposure. In an implementation, the UVC exposure manager 148 can control the intensity of the UVC radiation by controlling the number of UVC sources 124 & 140 activated (e.g., lamps), or by controlling power, volts, or amps to the UVC lamps. In an implementation, the UVC exposure manager 148 can control the intensity of the UVC radiation by controlling the distance between the lamps (or other UVC sources 124 & 140) and the surface of the wood product 104 being treated.

Example Processes

Customizing Wood Color and Lightness-Darkness

When describing modification of color and lightness-darkness in wood products 104, it can be helpful to define certain terms. In colorimetry and color theory, colorfulness, chroma, and saturation are related but distinct concepts referring to the perceived intensity of a specific color. Colorfulness is the visual sensation according to which the perceived color of an area appears to be more or less chromatic.

Chroma is the colorfulness relative to the brightness of a similarly illuminated area that appears to be white or highly transmitting. Therefore, chroma is not the same as colorfulness.

Saturation is the colorfulness of a color relative to its own brightness. Though this general concept is intuitive, terms such as chroma, saturation, purity, and intensity are often used without precision, and even when well-defined, these terms depend on the specific color model in use.

Thus a highly colorful wood product 104 is vivid and intense, while a less colorful wood product 104 appears more muted, and closer to gray. With no colorfulness at all, a color is a "neutral" gray (an image with no colorfulness in any of its colors is called grayscale). With three color appearance parameters—colorfulness (or chroma or saturation), lightness (or brightness), and hue—any color can be described.

The example system 100 can apply one or more of the following example general processes to modify appearance, color, texture, lightness, contrast, reflectivity, a grain feature, or a knot feature of a wood product:

Applying UVC to an untreated wood product at an angle, intensity, and duration to cause select changes in the appearance of the wood product;

Applying water to a wood product to modify the wood surface and then interacting UVC with the modified wood surface;

Applying a wood extract to a wood product to modify the wood product and then interacting UVC with the modified wood product and the wood extract to cause select changes in the appearance of the wood product;

Applying metal ions to a wood product to modify the wood product and then interacting UVC with the modified wood product and the metal ions to cause select changes in the appearance of the wood product;

Applying a wood extract to a wood product to modify the wood product, then applying metal ions to the wood product to modify the wood product, and then interacting UVC with the modified wood product, including the wood extract and the metal ions, to cause select changes in the appearance of the wood product;

Applying multiple agents, including optional pretreatments, to a wood product to modify the wood product, such as one or more of water, wood extracts, tannins, metal ions, salts, oxidizers, acids, bases, and so forth in various combinations to modify the wood products, and interacting UVC with the modified wood product and the multiple agents at various different stages of the process to cause select changes in the appearance of the wood product with each successive UVC exposure.

First Example Process

A first example process can be used with woods high in natural tannins, such as cedar and redwood. In an example implementation, untreated dry lumber is placed as the wood product 104 in the example system 100. The distance between the UVC sources 124 & 140 and the lumber is adjusted to achieve the desired effect. Typical distances are 6-20 inches above the surface of this wood product 104, for 40 watt lamps. The lumber wood product 104 may be exposed to the UVC radiation for 1-5 hours.

Second Example Process

A second example process can be used for woods high in natural tannins, such as cedar and redwood. The lumber wood product 104 first passes though the first spraying station 110 where water is spayed liberally over the lumber wood product 104 covering all surfaces. Resident times vary depending on the type and condition of the lumber. The excess standing water can be allowed to drain away and/or squeegeed off. The damp lumber is then processed with the UVC radiation. The distance between the UVC sources 124 & 140 is adjusted to achieve a desired effect. Typical distances are 6-20 inches above the surface. This lumber wood product 104 can be exposed to the UVC for 1-5 hours.

Third Example Process

A third example process can be used for wood products 104 that are low in natural occurring tannins, or to create custom color wood products 104. Wood extracts can be made via an aqueous or an alcohol extraction process. The wood extracts may also be purchased. In one implementation, the wood extract is a tannic acid solution used, for example, on a white oak wood product 104.

Tannic acid has a chemical formula of $C_{76}H_{52}O_{46}$ with a molecular weight of 1701.19 grams per mole, and a IUPAC name of 2,3-dihydroxy-5-({[(2R,3R,4S,5R,6R)-3,4,5,6-tetrakis({3,4-dihydroxy-5-[(3,4,5-trihydroxyphenyl)carbonyloxy]phenyl}carbonyloxy)oxan-2-yl]methoxy}carbonyl) phenyl 3,4,5-trihydroxybenzoate. Commercial tannic acid is extracted from one of the following plant parts: tara pods (*Caesalpinia spinosa*), gallnuts from *Rhus semialata* or *Quercus infectoria*, or Sicilian Sumac leaves (*Rhus coriaria*).

For example, a stock solution of tannic acid can be made according to model proportions of mixing in 10 grams of tannic acid powder for every 1000 ml of distilled water. The stock solution of tannic acid may be diluted tenfold and added to a reservoir of, for example, the third spraying station 126. A lumber wood product 104, for example, may be introduced into the third spraying station 126 and treated for approximately 10 minutes. The lumber wood product 104 is then removed from the spraying station and placed in the drying station 130 or a drying rack until substantially dry. Drying may be facilitated by fans in the drying station 130. The dry lumber wood product 104 is then subjected to UVC, for example under 40 watt mercury vapor UVC bulbs at a 6-20 inch distance, and treated for about 5 hours. After 5 hours the lumber wood product 104 is removed and can be stored. The concentration of the solutions above and the treatment times can be varied to achieve a desired effect.

Fourth Example Process

A fourth example process can be used for wood products 104 high in natural tannins, such as cedar and redwood. A stock solution of iron (II) chloride ($FeCl_2$) is prepared according to model proportions, such as dissolving 1 gram of iron (II) chloride in every 1000 ml of distilled water. Iron (II) chloride has a molecular weight of 126.75 grams per mole (anhydrous) or 198.81 grams per mole (tetrahydrate). Every 100 ml of the stock solution can be diluted to a final volume of 2 liters using distilled water. This working solution can be placed in a reservoir of the fourth spraying station 132. For example, a cedar lumber wood product 104 can be conveyed into the fourth spraying station 132 and treated with the solution for 5 minutes.

The lumber wood product 104 may be conveyed from the spraying station 132 into the fourth drying station 136 or onto a drying rack until dry. The substantially dry lumber wood product 104 is then conveyed into the second array 138 of UVC sources 140 and treated for about 5 hours. After 5 hours the lumber wood product 104 may be removed and stored. The concentrations of the solutions, and the treatment times, can be varied to achieve a desired effect.

Other metal ion solutions may be used in lieu of iron (II) chloride. For example, various concentrations the following may be applied to the wood product 104 prior to application of UVC radiation: a copper ion solution, a manganese ion solution, a nickel ion solution, a chromium ion solution, a calcium ion solution, a magnesium ion solution, a silver ion solution or colloid, a zinc ion solution, and a cobalt ion solution.

Fifth Example Process

A fifth example process can be used for wood products 104 that are low in natural occurring tannins, or to create custom color products. In this example process, a tannic acid solution is used, for example, on a white oak wood product 104. For example, a stock solution of tannic acid can be made according to model proportions of mixing in 10 grams of tannic acid powder for every 1000 ml of distilled water. The stock solution of tannic acid may be diluted tenfold and added to a reservoir of, for example, the third spraying station 126. The white oak wood product, such as lumber, is conveyed into the third spraying station 126 and treated for about 10 minutes. The example white oak wood product 104 is then removed from the third spraying station 126 and conveyed to the third drying station 130 or a drying rack until dry.

A stock solution of iron (II) chloride ($FeCl_2$) can be prepared according to model proportions, such as dissolving 1 gram of iron (II) chloride in every 1000 ml of distilled water. Every 100 ml of the stock solution can be diluted to a final volume of 2 liters using distilled water. This working solution can be placed in a reservoir of the fourth spraying station 132. The example white oak wood product 104 is then conveyed into the fourth spraying station 132 and treated for 5 minutes.

The example white oak wood product 104 is then conveyed from the fourth spraying station 132 and into the fourth drying station 136 or a drying rack until dry. The substantially dry white oak wood product 104 is then conveyed to the second array 138 of UVC sources 140, and irradiated with UVC for about 5 hours. After 5 hours the example white oak wood product 104 can be removed and stored. The concentrations of the solutions, and the treatment times, can be varied to achieve a desired effect.

Wood Pretreatment Methods

In the example system 100, various pretreatment techniques can be applied to a wood product 104, for example at the second spraying station 116, to achieve particular appearance results.

Acids

Acids, such as concentrated mineral acids, may be applied to a wood product 104 as a pretreatment before exposure of the wood and acid to UVC radiation. In an implementation, mineral acids are applied to degrade the surface of the wood product 104 (including lignins and cellulose) prior to application of other photoactive agents, such as wood extracts and metal ions, and subsequent exposure to UVC radiation. Applying mineral acids facilitates penetration of the metal and tannin solutions into the surface of the wood product 104, and promotes checking at the surface to increase surface area for increased exposure to the UVC radiation. Candidate acids include sulfuric acid, concentrated sulfuric acid, fuming sulfuric acid, nitric acid, hydrochloric acid, hydrobromic acid, hydroiodic acid; strong, moderate, and weak organic acids, such as acetic acid, glacial acetic acid, carboxylic acids, sulfonic acids; and other organic and inorganic acids that affect wood appearance upon exposure to or activation by UVC radiation.

In an example process, the wood product 104 is soaked with water, e.g., at the first spraying station 110, prior to the application of the acid to slow the initial reaction and facilitate a more uniform coverage. Concentrated sulfuric acid $H_2SO_4$ is applied to the surface of the wood product 104 and allowed to stand for 1-10 minutes (the time interval depending on the desired effect). Excess acid is neutralized with sodium bicarbonate or another neutralizer and then rinsed liberally with water, e.g., by the first rinsing station 112. The rinse may be tested to obtain a pH of approximately 7. The wood product 104 may be allowed to dry or actively dried by the first drying station 110 before proceeding with further treatments.

Bases

Bases may be used as a pretreatment on the surface of a wood product 104 to achieve saponification of surface oils for achieving a desired appearance of the wood product 104 after exposure to the UVC radiation.

In an implementation, strong bases, such as NaOH and KOH can be applied, e.g., by the second spraying station 116 to react with natural occurring wood oils and to degrade the wood (including lignins and cellulose) prior to application of other photoactive agents, such as wood extracts, metal ions, and subsequent exposure to UVC radiation. These caustic solutions react with the pitch and wood oils via saponification, and the resulting carboxylic acids salts or soaps can be readily washed away to facilitate subsequent penetration of the metal ions and tannin solutions as well as to promote checking at the surface of the wood product to increase surface area and increased exposure to the UVC radiation.

In an example process, the wood product 104 is soaked with water, e.g., at the first spraying station 110, prior to the application of the base to slow the initial reaction and facilitate a more uniform coverage. A concentrated base, such as 50% NaOH is applied to the surface of the wood product 104 and allowed to stand for 1-10 minutes (the time interval depending on the desired effect). Excess base may be neutralized, e.g., with a weak acid or with sodium bicarbonate, and rinsed liberally with water, e.g., by the first rinsing station 112. The rinse may be tested to obtain a pH of approximately 7. The wood product 104 may be allowed to dry or actively dried by the first drying station 110 before proceeding with further treatments.

Oxidizers

Oxidizers may be used as a pretreatment on the surface of a wood product 104 before other treatment steps. For example, hydrogen peroxide ($H_2O_2$) or a bleaching agent may be applied to react with naturally occurring wood oils and to degrade the wood (e.g., lignins and cellulose) prior to application of other photoactive agents, such as woods extracts and metal ions, before application of UVC radiation. Peroxide solutions may also react with the pitch and wood oils of the wood product 104 to lighten the base color of the wood product 104 to provide a lighter tint or a warmer tint to the color.

In an example process, the wood product 104 is soaked with water, e.g., at the first spraying station 110, prior to the application of the peroxide to slow the initial reaction and facilitate a more uniform coverage. A peroxide, such as 37% hydrogen peroxide is applied to the surface of the wood product 104 and allowed to dry. The wood product 104 may then be rinsed liberally with water, e.g., by the first rinsing station 112. The wood product 104 may be allowed to dry or may be actively dried by the first drying station 110 before proceeding with further treatments.

Example Methods

Figure 10:
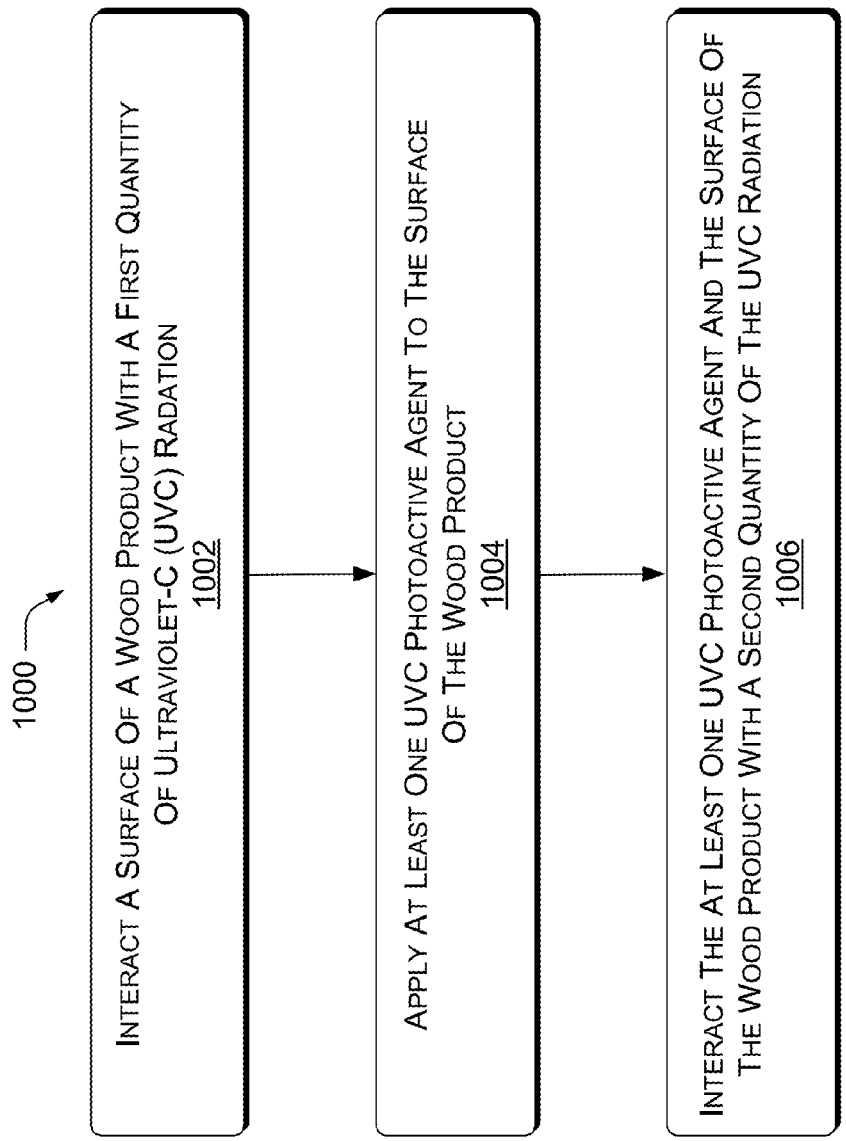
FIG. 10 is a flow diagram of an example method of modifying an appearance of a wood product by applying UVC radiation to a surface of the wood product and to a photoactive agent.

FIG. 10 shows an example method 1000 of modifying an appearance of a wood product. In the flow diagram, operations are shown in individual blocks. The example method 1000 may be performed by programmable hardware, such as the example system 100.

At block 1002, at least a surface of the wood product is interacted with a first quantity of ultraviolet-C (UVC) radiation.

At block 1004, at least one UVC photoactive agent is applied to the surface of the wood product.

At block 1006, the at least one photoactive agent and the surface of the wood product are interacted with a second quantity of the UVC radiation.

In an implementation, the example method 1000, prior to interacting the wood surface with the first quantity of UVC radiation, further includes applying a base, such as a 20% NaOH solution or a 20% KOH solution to the surface of the wood product, e.g., for approximately 1 minute, and rinsing the wood product with water to a neutral pH. The wood product may be soaked with water prior to applying the 20% NaOH solution or the 20% KOH solution.

In an implementation, the example method 1000, prior to interacting the wood surface with the first quantity of UVC radiation, further includes applying an oxidizer or peroxide, such as a 15-37% hydrogen peroxide ($H_2O_2$) solution to the surface of the wood product, e.g., for approximately 30 seconds. The wood product may be soaked with water prior to applying the 15-37% hydrogen peroxide solution.

In an implementation, the example method 1000, prior to interacting the wood surface with the first quantity of UVC radiation, further includes applying an acid to the surface of the wood product, e.g., for 1-30 seconds. The wood product may be soaked with water prior to applying the acid. The acid may be sulfuric acid, concentrated sulfuric acid, fuming sulfuric acid, nitric acid, hydrochloric acid, hydrobromic acid, hydroiodic acid; strong, moderate, and weak organic acids, such as acetic acid, glacial acetic acid, carboxylic acids, and sulfonic acids; or other mineral, organic, or inorganic acids. After the 1-30 seconds, the acid may be neutralized on the surface of the wood with sodium bicarbonate or a base, and the surface of the wood rinsed with water and dried.

Figure 11:
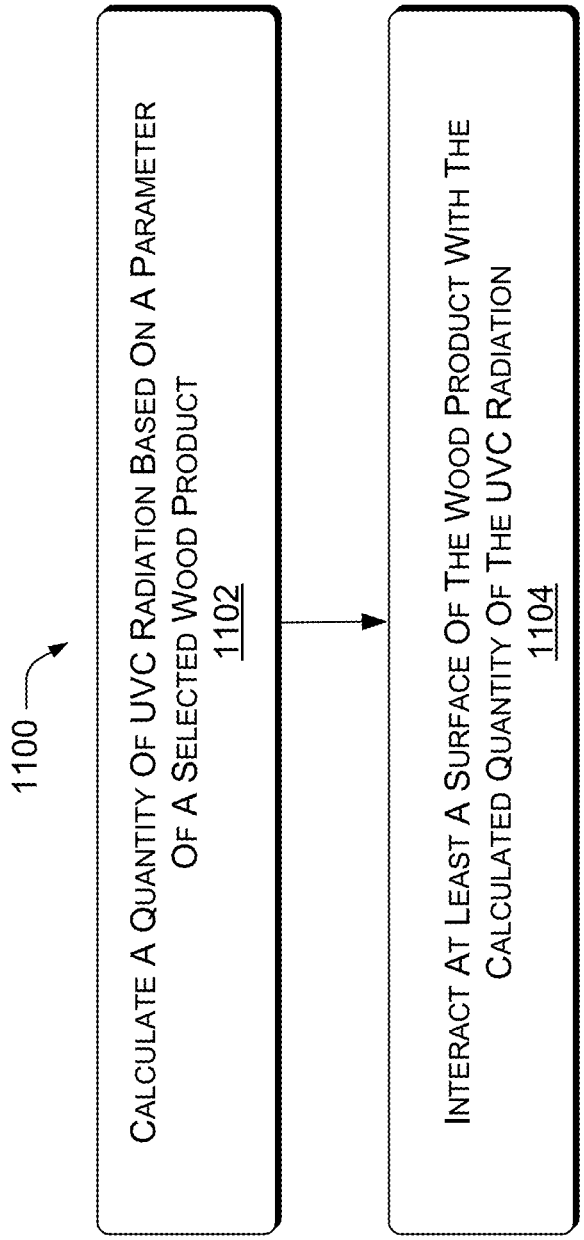
FIG. 11 is a flow diagram of an example method of modifying an appearance of a wood product by applying UVC radiation to a surface of the wood product.

FIG. 11 shows an example method 1100 of modifying an appearance of a wood product. In the flow diagram, operations are shown in individual blocks. The example method 1100 may be performed by programmable hardware, such as the example system 1100.

At block 1102, a wood product is selected, and a quantity of UVC radiation is calculated based on a parameter of the selected wood product.

At block 1104, at least a surface of the wood product is interacted with the calculated quantity of the UVC radiation.

For example, the quantity of the UVC radiation may be calculated based on an example parameter such as: an identity of the wood, an age of the wood, a density of the wood, a hardness or softness of the wood, a tensile strength of the wood, whether the wood is from an angiosperm or a gymnosperm, a cellulose content of the wood, a tannin content of the wood, a lignin content of the wood, an oil content of the wood, a structure of the wood, a grain of the wood, grain direction of the wood, a grain density of the wood, a straightness of the wood, a surface smoothness of the wood, a surface texture of the wood, a wetness or dryness of the wood, a hygroscopicity of the wood, a capacity to absorb water of the wood, a knottiness of the wood, a state of decay of the wood, a radiation absorptivity of the wood, a surface area of the wood, a color of the wood, or a brightness of the wood.

In an implementation, the example method 1100, prior to interacting the wood surface with the first quantity of UVC radiation, may further include applying a base, such as a 20% NaOH solution or a 20% KOH solution to the surface of the wood product, e.g., for approximately 1 minute, and rinsing the wood product with water to a neutral pH. The wood product may be soaked with water prior to applying the 20% NaOH solution or the 20% KOH solution.

In an implementation, the example method 1100, prior to interacting the wood surface with the first quantity of UVC radiation, further includes applying an oxidizer or a peroxide, such as a 15-37% hydrogen peroxide ($H_2O_2$) solution to the surface of the wood product, e.g., for approximately 30 seconds. The wood product may be soaked with water prior to applying the 15-37% hydrogen peroxide solution.

In an implementation, the example method 1100, prior to interacting the wood surface with the first quantity of UVC radiation, further includes applying an acid to the surface of the wood product, e.g., for 1-30 seconds. The wood product may be soaked with water prior to applying the acid. The acid may be sulfuric acid, fuming sulfuric acid, nitric acid, hydrochloric acid, hydrobromic acid, hydroiodic acid; or a strong, moderate, or weak organic acid, such as acetic acid, glacial acetic acid, a carboxylic acid, or a sulfonic acid; or another mineral, organic, or inorganic acid. After the 1-30 seconds, the acid may be neutralized on the surface of the wood with sodium bicarbonate or a base, and the surface of the wood rinsed with water and dried.

Figure 12:
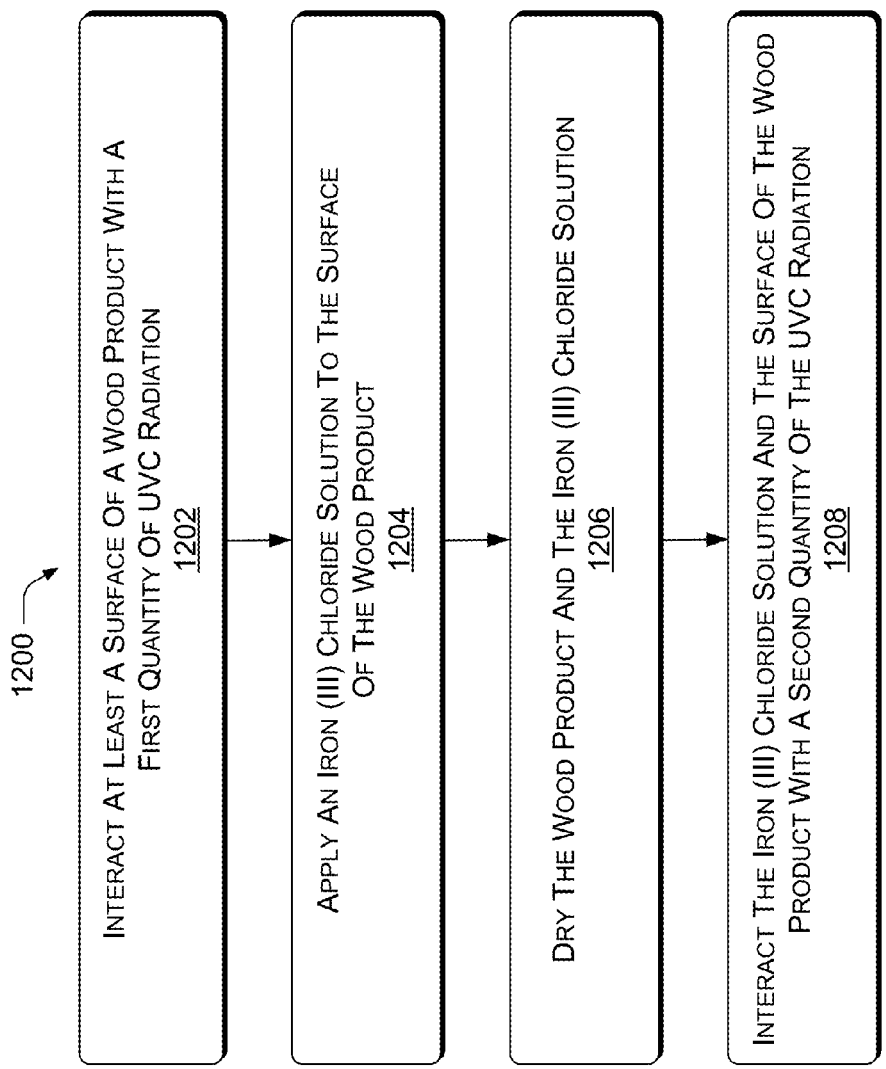
FIG. 12 is a flow diagram of an example method of modifying an appearance of a wood product by applying a metal ion photoactive agent to the wood product and by applying UVC radiation to the metal ion photoactive agent and to the surface of the wood product.

FIG. 12 shows an example method 1200 of modifying an appearance of a wood product. In the flow diagram, operations are shown in individual blocks. The example method 1200 may be performed by programmable hardware, such as the example system 100.

At block 1202, at least a surface of the wood product is interacted with a first quantity of ultraviolet-C (UVC) radiation equivalent to a one hour exposure to 40 watt UVC sources at a distance of approximately 6 inches.

At block 1204, a UVC photoactive agent is applied to the surface of the wood product, wherein the UVC photoactive agent comprises a 0.5-5.0% alcohol-based ferric chloride (iron (III) chloride or $FeCl_3$) solution.

At block 1206, the wood product is allowed to dry.

At block 1208, the UVC photoactive agent and the surface of the wood product are interacted with a second quantity of the UVC radiation equivalent to a four hour exposure to 40 watt UVC sources at a distance of approximately 6 inches.

A 0.5-5.0% $FeCl_3$ solution may be prepared, for example, by dissolving 0.50-5.0 grams of $FeCl_3$ in every 100 ml of 91% isopropyl alcohol.

Figure 13:
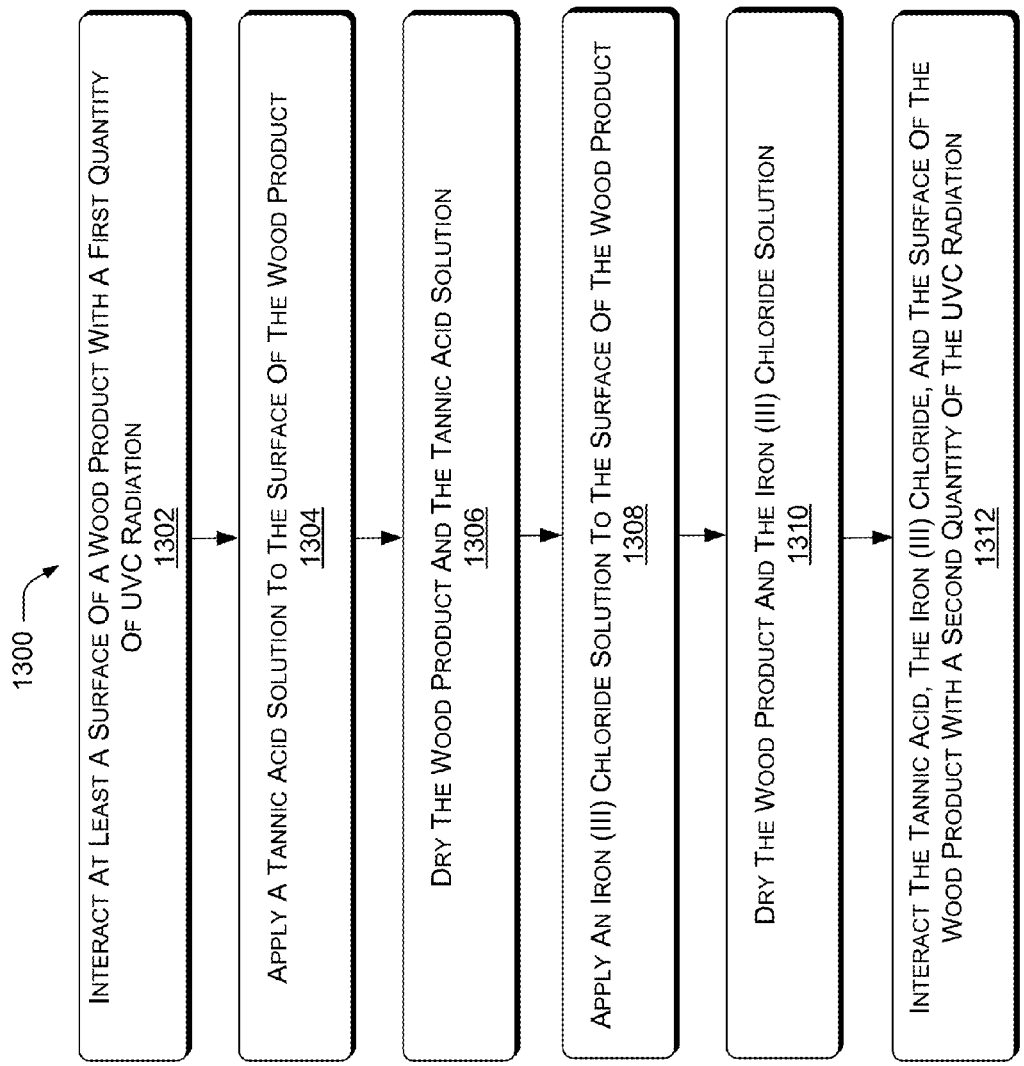
FIG. 13 is a flow diagram of an example method of modifying an appearance of a wood product by applying a wood extract photoactive agent and a metal ion photoactive agent to the wood product and by applying UVC radiation to the wood extract photoactive agent, to the metal ion photoactive agent, and to the surface of the wood product.

FIG. 13 shows an example method 1300 of modifying an appearance of a wood product. In the flow diagram, operations are shown in individual blocks. The example method 1300 may be performed by programmable hardware, such as the example system 100.

At block 1302, at least a surface of the wood product is interacted with a first quantity of UVC radiation equivalent to a one hour exposure to 40 watt UVC sources at a distance of approximately 6 inches.

At block 1304, a first UVC photoactive agent is applied to the surface of the wood product, wherein the first UVC photoactive agent comprises a 2% tannic acid solution.

At block 1306, the wood product is allowed to dry.

At block 1308, a second UVC photoactive agent is applied to the surface of the wood product, wherein the second UVC photoactive agent comprises a 0.5-5.0% alcohol-based ferric chloride (iron (III) chloride) solution.

At block 1310, the wood product is allowed to dry.

At block 1312, the first and second UVC photoactive agents and the surface of the wood product are interacted with a second quantity of the UVC radiation equivalent to a four hour exposure to 40 watt UVC sources at a distance of approximately 6 inches.

Figure 14:
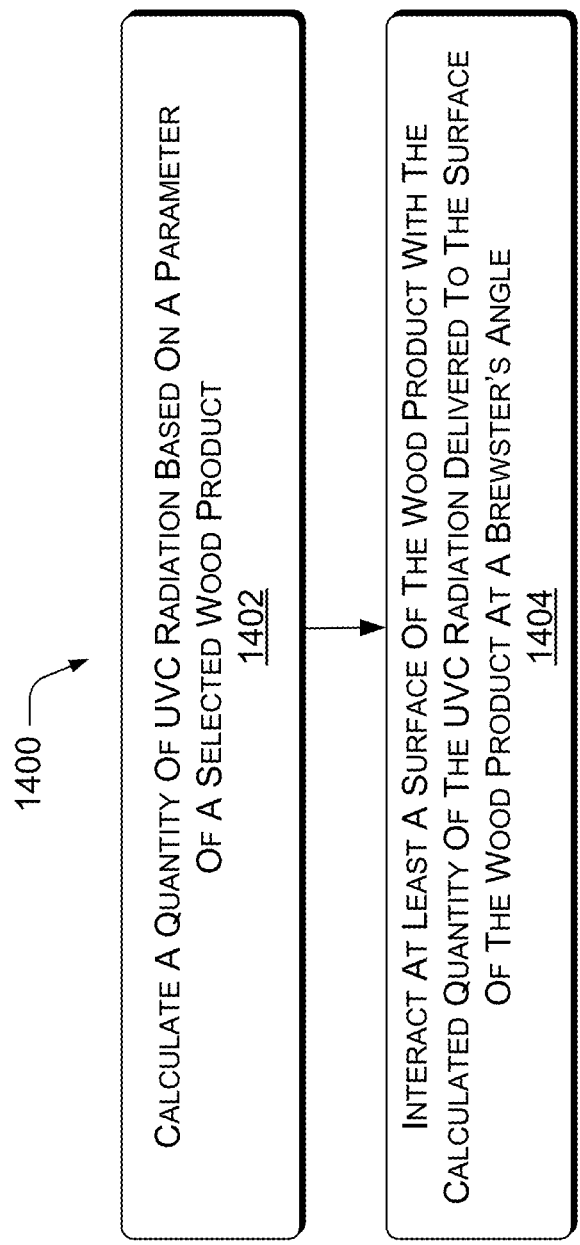
FIG. 14 is a flow diagram of an example method of modifying an appearance of a wood product by applying UVC radiation to a surface of the wood product at a Brewster's angle.

FIG. 14 shows an example method 1400 of modifying an appearance of a wood product. In the flow diagram, operations are shown in individual blocks. The example method 1400 may be performed by programmable hardware, such as the example system 100.

At block 1402, a wood product is selected, and a quantity of UVC radiation is calculated based on a parameter of the selected wood product.

At block 1404, at least a surface of the wood product is interacted with the calculated quantity of the UVC radiation delivered to the surface of the wood product at a Brewster's angle.

FIG. 15 shows an example method 1500 of modifying an appearance of a wood product. In the flow diagram, operations are shown in individual blocks. The example method 1500 may be performed by programmable hardware, such as the example system 100.

At block 1502, a wood product is selected, and a quantity of UVC radiation is calculated based on a parameter of the selected wood product.

At block 1504, at least a surface of the wood product is interacted with the calculated quantity of the UVC radiation delivered to the surface of the wood product at an acute angle against a grain direction of the surface of the wood product, wherein only one side of the grain interacts with the UVC radiation.

CONCLUSION

Although a few embodiments of the disclosure have been described in detail above, those of ordinary skill in the art will readily appreciate that many modifications are possible without materially departing from the teachings of this disclosure. Accordingly, such modifications are intended to be included within the scope of this disclosure as defined in the claims.

The invention claimed is:

1. A system, comprising:
an array of ultraviolet-C (UVC) radiation sources; and
a conveyor for transporting a wood product under the array of UVC sources to interact a UVC radiation with a surface of the wood product for modifying an appearance, color, texture, lightness, contrast, reflectivity, grain feature, or knot feature of the wood product.

2. The system of claim 1, wherein the array of UVC radiation sources comprises UVC sources selected from the group consisting of mercury vapor lamps, UVC flash lamps, one or more UVC lasers, one or more UVC pulsed fiber lasers, UVC laser diodes, carbon arc UVC sources, and UVC light emitting diodes (LEDs).

3. The system of claim 1, further comprising multiple irradiating stations each irradiating station comprising an array of the UVC sources to interact with the surface of the wood product at multiple stages of a process for modifying an appearance, color, texture, lightness, contrast, reflectivity, grain feature, or knot feature of the wood product.

4. The system of claim 1, further comprising a first spraying station for applying water to the wood product prior to interacting the surface of the wood product with a first quantity of the UVC radiation;
a second spraying station for applying at least one pretreatment solution to the surface of the wood products;
a third spraying station for applying a first photoactive agent to the surface of the wood product after interacting the surface of the wood product with the first quantity of the UVC radiation;
a fourth spraying station for applying a second photoactive agent to the surface of the wood product prior to interacting the surface of the wood product with a second quantity of the UVC radiation.

5. The system of claim 4, wherein the pretreatment solution is selected from the group consisting of a NaOH solution, a KOH solution, a hydrogen peroxide solution, sulfuric acid, fuming sulfuric acid, nitric acid, hydrochloric acid, hydrobromic acid, hydroiodic acid, an organic acid, acetic acid, glacial acetic acid, a carboxylic acid, and a sulfonic acid.

6. The system of claim 5, wherein the second spraying station applies a water rinse to the surface of the wood product after applying the pretreatment solution.

7. The system of claim 4, wherein the first photoactive agent is selected from the group consisting of a tannin solution, a tannic acid solution, a wood lignin solution, a wood extract solution, a cellulose solution, and a wood oil solution.

8. The system of claim 7, wherein the third spraying station applies a water rinse to the surface of the wood product after applying the first photoactive agent.

9. The system of claim 4, wherein the second photoactive agent is selected from the group consisting of a metal ion solution, an iron ion solution, a copper ion solution, a manganese ion solution, a nickel ion solution, a chromium ion solution, a calcium ion solution, a magnesium ion solution, a silver ion solution or colloid, a zinc ion solution, and a cobalt ion solution.

10. The system of claim 9, wherein the fourth spraying station applies a water rinse to the surface of the wood product after applying the second photoactive agent.

11. The system of claim 4, further comprising at least one drying station for drying the surface of the wood product after the first spraying station, the second spraying station, the third spraying station, or the fourth spraying station.

12. The system of claim 1, further comprising aluminum reflectors to reflect and concentrate the UVC radiation for interacting with the surface of the wood product.

13. The system of claim 1, wherein the array of UVC radiation sources is disposed to direct the UVC radiation to the surface of the wood product only at a Brewster's angle.

14. The system of claim 1, wherein the array of UVC radiation sources is disposed to direct the UVC radiation at an acute angle against a grain of the surface of the wood product.

15. The system of claim 1, further comprising a geodesic chamber housing the array of UVC radiation sources to expose multiple sides of a 3-dimensional wood product to the UVC radiation.

* * * * *